United States Patent [19]

Falco

[11] Patent Number: 4,867,149
[45] Date of Patent: Sep. 19, 1989

[54] EARPLUGS

[75] Inventor: Robert N. Falco, Indianapolis, Ind.

[73] Assignee: Cabot Corporation, Waltham, Mass.

[21] Appl. No.: 285,339

[22] Filed: Dec. 16, 1989

Related U.S. Application Data

[63] Continuation of Ser. No. 945,174, Dec. 22, 1986, abandoned, which is a continuation of Ser. No. 717,371, Mar. 29, 1985, abandoned.

[51] Int. Cl.$^4$ .............................................. A61F 11/02
[52] U.S. Cl. .................................................. 128/864
[58] Field of Search ................ 128/152, 151; 181/130, 181/135

[56] References Cited

U.S. PATENT DOCUMENTS

| Re. 28,560 | 9/1975 | Fling | 128/152 |
| D. 253,723 | 12/1979 | Leight | 128/152 |
| 2,246,737 | 6/1941 | Knudsen | 128/152 |
| 2,393,005 | 1/1946 | Veneklasen | 128/152 |
| 2,427,664 | 9/1947 | Dunbar et al. | 128/152 |
| 2,487,038 | 11/1949 | Baum | 128/152 |
| 2,619,960 | 12/1952 | Reynolds | 128/152 |
| 2,670,738 | 3/1954 | Gibbons | 128/152 |
| 3,800,791 | 4/1974 | Visor | 128/152 |
| 4,034,749 | 7/1977 | Von Kesseru et al. | 128/130 |
| 4,353,364 | 10/1982 | Woods | 128/152 |
| 4,540,063 | 9/1985 | Ochi et al. | 128/152 |

FOREIGN PATENT DOCUMENTS 578485 6/1959 Canada ................................. 128/152

OTHER PUBLICATIONS

General Electric, "Peacekeeper ® Personalized Hearing Protectors", MD0-200, 1971.

Primary Examiner—John D. Yasko

[57] ABSTRACT

There is disclosed herein a multiple flange earplug composed of a resilient soft polymeric material.

17 Claims, 1 Drawing Sheet

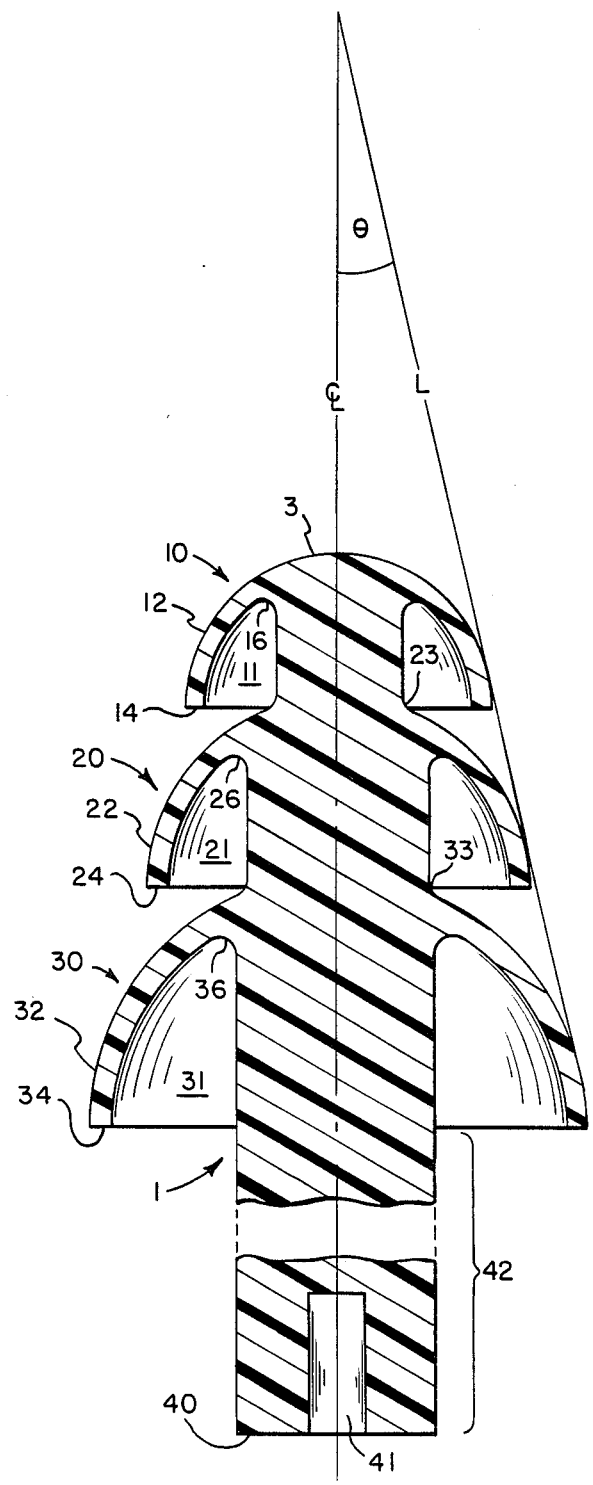

EARPLUGS

This is a continuation of copending application Ser. No. 945,174, filed on Dec. 22, 1986, now abandoned, which is a continuation of application Ser. No. 717,371, filed Mar. 29, 1985, now abandoned.

BACKGROUND OF THE INVENTION

1. Field of the Invention

The present invention relates broadly to earplugs and is more specifically directed to a resilient polymeric multiple flange earplug construction useful as a hearing protector.

2. The Prior Art

In the United States one of the better known earplugs of the general type contemplated by the present invention is that known as the "V-51 R", the construction details of which earplug are disclosed in a report entitled *Development of an Extra Small and Extra Large Size for the V-51 R Earplug*, D. T. Blackstock and H. E. Von Gierke, April 1956, Aero Medical Laboratory, Wright Air Development Center, Air Research and Development Command, United States Air Force, WADC Technical Report 56-142. This earplug was developed during the course of World War II in order to provide improved hearing protection to members of the military who are subjected to concussive sounds, such as gunfire or explosions or to extremely noisy work environments, such as at airports or aircraft maintenance facilities. The V-51 R earplug is composed of a resilient elastomeric material, such as neoprene rubber, and comprises a single retroverted flange element extending from the nose end of a tubular rubber stalk member. The flange element extends rearwardly from the nose of the tubular rubber stalk and is so spaced therefrom as to provide a free annular space therebetween. In use, the earplug is forceably inserted into the ear canal, thereby at least partially collapsing the rearwardly extending flange element into the underlying free annular space and conforming said flange element into an acoustic sealing relationship with the constraining walls of the ear canal.

In U.S. Pat. No. 2,427,664, J. Y. Dunbar and J. S. Knight, Sept. 23, 1947 and U.S. Pat. No. 2,717,596, J. S. Knight, Sept. 13, 1955, there are disclosed earplugs similar to the V-51 R earplug described in the aforementioned Blackstock et al. report. In FIGS. 2 and 3 of U.S. Pat. No. 2,427,664, there is additionally depicted an earplug comprising four disk-shaped flange elements of serially increasing diameters extending substantially transversely of the supporting stalk member. As is most clearly seen in FIG. 3, all four flange elements of the construction are disclosed to be insertable into the ear canal and are biased somewhat rearwardly by the constraining walls thereof.

Unfortunately, earplugs of the type disclosed in the foregoing publications and in those variants thereof known to the present applicant are often possessed of several disadvantages. Firstly, when properly worn a certain significant proportion of the wearer population often experiences discomfort in the use of such plugs. Generally this discomfort is perceived as a sense of excessive pressure being brought to bear on the walls of the ear canals, which pressure can be of such magnitude as to be painful. A common user response to such discomfort is to withdraw the offending earplug from the ear canal to the point where the perceived excessive pressure is relieved and, when this is done, as often as not the acoustic seal between the plug and the ear canal is broken or weakened, thereby destroying or at least compromising the intended hearing protection function of the earplug. This is a particularly pernicious deficiency because, while the subject person involved may seem from outward appearances to be suitably hearing protected in fact, he or she may not be protected at all. Secondly, due to the well known anatomic variability of sizes and shapes of ear canals throughout the population, including the variability which often exists as between the ear canals of an individual user and the variations in size of individual ear canals which occur naturally, it is generally required that flanged earplugs be produced in a number of sizes and that they be carefully fitted by trained personnel in order to assure the attainment of competent hearing protection. For instance, the V-51 R plug mentioned above is presently produced in five different discrete sizes which, according to the aforementioned Blackstock et al. report, provides the ability to properly fit 80-85% of the adult male user population therewith. Obviously, the requirement to produce multiple sizes of an earplug adds greatly to the cost and complexity of manufacture thereof. In accordance with the present invention, however, there is provided a multiple flange earplug which can be produced in a single size and yet comfortably fit and provide effective hearing protection for the great majority of the population.

OBJECTS OF THE INVENTION

It is a principal object of the present invention to provide a new and novel multiple flange earplug.

It is another object of the invention at once to provide a novel multiple flange earplug construction which is comfortable to wear properly and which provides competent acoustic sealing of the ear canals.

It is still another object of the invention to provide a novel multiple flange earplug construction which may be produced in a single size and which earplug will properly and comfortably fit up to 98% of the entire adult user population.

It is still another object of the invention to provide a novel multiple flange earplug construction wherein the flange elements may be readily manipulated to expose normally hidden portions of the earplug such as for purposes of cleansing thereof.

Other objects and advantages of the present invention will in part be obvious and will in part appear hereinafter.

SUMMARY OF THE INVENTION

In accordance with the invention there is provided a multiple flange earplug composed of a resilient soft polymeric material, said earplug comprising a stalk member carrying thereon an array of at least three hollow rearwardly directed and spaced apart flange elements of substantially circular cross sections, the first of which elements extends from the nose end of the stalk member. Each of the flange elements of the array comprises a skirt of relatively thin uniform thickness and is composed of a soft resilient polymeric material having a Shore A Durometer hardness value of between about 10 and about 90. The flange elements of the array increase serially in diameter, starting from the nose end of the stalk member. The diameter of the stalk member underlying each flange element is selected to provide an annular free space between the inner surface of the skirt of the associated flange element and the stalk member of sufficient dimension as to allow said skirt portion to collapse into and occupy said space upon insertion of the earplug into the ear canal.

BRIEF DESCRIPTION OF THE DRAWING

The drawing forming part hereof is a schematic, diagrammatic longitudinal sectional view of an earplug in accordance with the invention, including various preferred embodiments thereof.

DESCRIPTION OF THE PREFERRED EMBODIMENTS

Reference being made to the drawing hereof, the earplug of the invention broadly comprises a stalk member 1 and an array of at least three rearwardly oriented and spaced apart flange elements 10, 20 and 30, each being of generally circular cross section. Preferably, each flange element of the array extends rearwardly from its point of attachment to the stalk member 1 in a convexly arcuate manner and, most preferably, will be of generally hemispherical conformation. By "generally hemispherical" it is meant that the flange element defines no less than about 45% and no more than about 55% of a chordally sectioned hollow spherical body whose external surface is, at essentially all points thereon, substantially equidistant from the single geometric center thereof. The earplug of the invention can be fabricated by any suitable polymer molding technique, such as by injection molding thereof. An essential to the attainment of the benefits of the invention is the selection of the resilient polymeric material utilized in the fabrication of at least the skirts 12, 22 and 32 of flange elements 10, 20 and 30. Said material should have a Shore A Durometer hardness value (by the technique of ASTM 2240-81) of between about 10 and about 90 and, preferably, of between about 30 and about 60. The stalk member 1 can, of course, be composed of a resilient polymeric material of the same type employed for the flange skirts 12, 22 and 32 elements or, if desired, can be composed of a resilient polymeric material having a somewhat higher Shore A Durometer hardness value of, say, up to about 100. In one preferred embodiment of the invention, the material of construction of the stalk member 1 will have a Shore A Durometer hardness value of between about 50 and about 70. In another preferred embodiment of the invention, however, for purposes of easy fabrication, it will be preferred to utilize a single polymeric material for the entirety of the construction.

Obviously, there are many known resilient polymeric materials which may be utilized effectively in the fabrication of the earplugs of the invention. For instance, natural rubber, neoprene rubber, SBR rubber, silicone rubber, EPDM rubber, polybutadiene rubber, polyurethane elastomers, ethylene vinyl acetate elastomers, elastomers based on acrylic acid precursors and vinyl halide polymers are all generally suitable materials of construction which can generally be procured from commercial sources with the necessary Shore A Durometer values or which can be suitably compounded (such as by internal and/or external plasticizing thereof) so as to confer the necessary hardness values thereto. Particularly preferred polymeric materials are the thermoplastic silicone rubber compositions such as exemplified by a family of thermoplastic injection moldable elastomers sold under the trademark, C-FLEX ®, Concept Polymer Technologies, Inc., Clearwater, Fla. These silicone rubber compositions are available in a considerable range of Shore A Durometer hardness values, can be thermally formed into intricate shapes by any conventional thermoplastic molding technique and the wares produced therefrom can generally be sterilized or cleansed without degradation thereof. Another preferred material of construction of the earplugs of the invention is a thermoplastic SBR block copolymer such as produced and sold in a number of grades under the brand name, KRATON, by Shell Chemical Company, Synthetic Rubber Division, NY, NY.

The first flange element 10 extends outwardly and rearwardly from the nose end 3 of stalk member 1, thereby to define a uniformly thin skirt 12 which is spaced apart along its length from that portion of stalk member 1 lying thereunder. The second flange element 20 extends outwardly and rearwardly from a first intermediate location along the length of stalk member 1, thereby to define a uniformly thin skirt 22 which is spaced apart along its length from that portion of stalk member 1 lying thereunder. Similarly, the third flange element 30 extends outwardly and rearwardly from a second intermediate location along the length of stalk member 1, thereby to define a uniformly thin skirt 32 which is spaced apart along its length from that portion of stalk member 1 lying thereunder. As will be noted from the drawing, the root portions 16, 26 and 36 of flange skirts 12, 22 and 32 respectively, in other words, the points of juncture of the interior surfaces of said skirts with the stalk member 1, are preferably conformed such as to provide minimum radiusing therebetween consistent with good molding practices, thereby to minimize thickening and consequential stiffening of the material of construction at said points. This design feature of the construction not only assures that the skirts 12, 22 and 32 are afforded maximum flexibility at said root portions, but also provides the skirts 12, 22 and 32 with a desirable "over center" eversion capability whereby each skirt can be readily manipulated so as to be everted from its normally rearwardly directed orientation to a forwardly directed orientation. When so forwardly everted, the interior surfaces of said skirts and the portions of the stalk member 1 normally underlying said skirts are exposed, thereby affording the user with the ability to readily inspect and/or cleanse areas of the earplug normally hidden from view.

It is also to be noted that the diameters of the hollow flange elements 10, 20 and 30 increase serially and that, in a preferred embodiment of the invention, said elements are spaced along the length of stalk member 1 such that, in the finished earplug, a single straight line of construction, L, can be drawn so as to be in at least point contact with all flange elements of the array. In this preferred embodiment, said diameters and spacing are also selected such that the half-angle $\theta$ defined between said line of construction L and the forwardly extended centerline $C_L$ of the stalk member 1 will reside within the range of between 10° and 16°, the preferred range for the half-angle $\theta$ being between about 12° and about 14°. By adherence to these dimensional criteria it is assured that the earplug constructed in accordance therewith will be utilizable by and effective for the great majority of the user population. For instance, where the half-angle $\theta$ is 13°, the flange elements are generally hemispherical and the radius of the first flange element 10 is about 0.165 inch (4.19 mm), it has been found that the earplug of the invention can produce acoustically effective seals for up to 98% of the entire adult user population, including females. Also, it is helpful in this regard that the spacing between flange elements 10, 20 and 30 along the stalk member 1 be such that the trailing edges 14 and 24 of the skirts 12 and 22 each be coplanar to or, even more preferably, be slightly overlying the nose end of the succeeding flange element thereto.

It will be apparent to those of skill in the art that many of the functional benefits of the present invention arise, at least in part, because the flange elements of the construction are embued with the ability to resiliently deform, in use, to the extent necessary under relatively small and essentially linear forces exerted by or reflected into the walls of the ear canal upon insertion of the earplug thereinto. Thus, there exists a complex interplay between the specific geometries and sizing of the elements of the earplug construction taken in combination with the hardness(es) of the resilient polymeric material(s) of construction employed therefor. Accordingly, it is not only important that the material of construction employed for each of the skirts 12, 22 and 32 have a Shore A Durometer hardness value of between about 10 and about 90, but it is also important that the thickness of each of said skirts 12, 22 and 32 fall within the range of from about 0.008 (0.20 mm) and about 0.050 inch (1.27 mm). While no hard and fast rule of construction can be set in this regard, generally speaking the softer the material of construction the greater can be the thickness of the skirt 12, 22 or 32. Where materials of construction falling within the preferred range of Shore A Durometer hardness values of between about 30 and about 60 are employed, it has been found that the benefits of the invention are generally substantially forthcoming when the thickness of each of the skirts 12, 22 and 32 is within the range of 0.030 inch (0.76 mm) and 0.012 inch (0.30 mm). Obviously, the proper balancing of thickness of each of the skirts 12, 22 and 32 and the Shore A durometer hardness value of the resilient polymeric material of construction thereof can be readily determined experimentally. In a preferred embodiment of the invention, it has been found that a nominal thickness of about 0.020 inch (0.50 mm) of each of the skirts 12, 22 and 32 and the use therefor of a resilient polymeric material of construction having a Shore A Durometer hardness value of about 40 yields an earplug construction having an excellent overall combination of effective acoustic sealing and wearer comfort properties.

As mentioned previously, the diameter of that portion of the stalk member underlying each of the skirts 12, 22 and 32 of the flange elements 10, 20 and 30, respectively, is selected such as to provide an annular free space 11, 21 or 31 thereunder and into which free space said skirt is enabled to deflect during insertion of the earplug into the ear canal. The specific dimensions of the annular free spaces 11, 21 and 31 are not particularly critical provided, of course, that each be adequate to serve the foregoing function. It is, however, generally desirable that each said annular free space have a dimension thereacross, determined by subtracting the diameter of the underlying stalk member from the internal diameter of the open end of the skirt and dividing the result by two, of at least twice the thickness of the particular skirt 12, 22, or 32 disposed thereover. By "annular free space", it is meant that the annular space 11, 21 or 31 contain no element or material therein which would tend to obstruct or restrict the movement of the associated skirt thereinto.

Bearing the foregoing in mind, it is within the ambit of the invention to form the stalk member 1 of a single uniform diameter. Where this is done, however, it will be obvious that due consideration of the annular free space underlying each flange skirt will ordinarily dictate that the uniform diameter selected for the stalk member 1 will be based upon consideration of the annular free space for the smallest skirt, in other words, the skirt 12 of the nose flange element 10. Thus, unless the contemplated constant diameter stalk member is formed from a relatively stiff resilient polymeric material, such as one having a Shore A Durometer hardness value of greater than about 50, it can be found that the resulting earplug construction can be somewhat flaccid along the stalk member 1 and that said stalk member does not provide sufficient support for the second and third flange elements 20 and 30 as to permit them to be readily inserted into the ear canal solely by manipulation of the stalk member. For these reasons, then, it is generally preferred that the diameter of the stalk member 1, particularly where it is formed of a material of construction having a Shore A Durometer hardness value of less than about 50, be progressively or serially increased rearwardly from flange element to flange element, thereby to progressively or serially stiffen that portion of said member supporting the flange elements thereon.

In order that the earplugs of the invention can be readily inserted and removed from the ear canal, it is desirable that the stalk member 1 extend rearwardly to any convenient length beyond the trailing edge 34 of the rearmost flange element 30 such that the rearmost portion thereof defines a handle 42 to be readily grasped between the thumb and forefinger of the user.

It is often desirable to provide pairs of earplugs tethered together by means of a length of pliant cord. Such a tethered earplug construction can serve to prevent accidential dropping or loss thereof. This can be of importance, for instance, where the earplugs are to be utilized in an industrial food processing environment or in an environment wherein a dropped earplug would be likely to be so dirtied as to be rendered unusable or to be lost altogether. In order to provide such a tethered earplug construction, the free end 40 of stalk member 1 can be provided with an axially oriented channel or aperture 41 of a size adapted to receive the end of a length of a pliant cord (not shown) therein. Said cord can be secured in the channel or aperture 41 by any suitable means, such as by solvent or thermal welding thereof or by use of a suitable adhesive or by use of a cord whose ends are of somewhat greater diameter than the diameter of the receiving channel or aperture 41, thereby to cause the resilient polymeric material surrounding said channel or aperture 41 to resiliently grasp the cord ends in a secure manner. For further general details relating to tethered earplug constructions reference may be had to such literature as: U.S. Pat. No. D-241,881, to Peterson et al.; U.S. Pat. No. 4,193,396, to Wacker; U.S. Pat. No. 4,219,018, to Draper, Jr.; U.S. Pat. No. D-245,202, to Asker.

Additionally, while earplugs in accordance with the present invention may, as hereinbefore indicated, be utilized as individual ear insertable wares, they may also be utilized as stopple elements of a hearing protector device comprising a generally U-shaped spring headband to the free ends of which headband the stopple elements are affixed in an inwardly directed manner. In this embodiment, the earplugs of the invention are inserted into the ear canals of the wearer and are maintained under the continuous inwardly directed biasing forces of the spring headband. Further details relating to hearing protectors of this general type can be had by reference to such literature as U.S. Pat. No. 4,461,290, to Gardner, Jr. et al., or U.K. Pat. No. 1,355,052, to Metal Box Company, Limited.

Utilizing the foregoing principles of construction and for illustrative, non-limiting exemplary purposes, a plurality of three-flange earplugs substantially conforming to the drawing hereof was produced by injection molding of a thermoplastic silicone rubber (C-FLEX ® elastomer) having a Shore A Durometer hardness value of about 40. Referring to the drawing, the dimensions of the earplugs so produced are set forth below:

| | | |
|---|---|---|
| Overall length of stalk member 1 | 1.183 inches | (30.05 mm) |
| Diameter of stalk member 1 at end 40 | 0.203 inch | (5.15 mm) |
| Diameter of stalk member 1 underlying skirt 32 | 0.203 inch | (5.15 mm) |
| Diameter of stalk member 1 underlying skirt 22 | 0.188 inch | (4.78 mm) |
| Diameter of stalk member 1 underlying skirt 12 | 0.134 inch | (3.40 mm) |
| Radius of hemispherical flange element 10 | 0.165 inch | (4.19 mm) |
| Radius of hemispherical flange element 20 | 0.203 inch | (5.15 mm) |
| Radius of hemispherical flange element 30 | 0.255 inch | (6.48 mm) |
| Axial length of hemispherical flange element 10 | 0.174 inch | (4.42 mm) |
| Axial length of hemispherical flange element 20 | 0.206 inch | (5.23 mm) |
| Axial length of hemispherical flange element 30 | 0.262 inch | (6.65 mm) |
| Thickness of skirts 12, 22 and 32, each | 0.019 inch | (0.48 mm) |
| Length, nose 3 to nose 24 | 0.385 inch | (9.78 mm) |
| Length, nose 3 to nose 34 | 0.649 inch | (16.48 mm) |
| Annular space 11 | 0.085 inch | (2.16 mm) |
| Annular space 21 | 0.090 inch | (2.28 mm) |
| Annular space 31 | 0.135 inch | (3.43 mm) |
| Half-angle θ | 13° | |

The earplugs were tested in accordance with the test procedure of ANSI S3.19-1974, utilizing ten subjects. In the first test series (hereinafter "Maximum Comfort Test") the subjects were instructed to insert the plugs into their ear canals only to the point of maximum perceived wearer comfort. In the second test series (hereinafter "Maximum Attenuation Test") the subjects were individually fitted by a trained technician to the point of maximum acoustic sealing of the ear canals by the plugs. The Maximum Comfort Test yielded an NRR value of 22 while the Maximum Attenuation Test yielded an NRR value of 25. During the course of the Maximum Comfort Test the subjects were asked to assess the relative comfort of the fitted earplugs in accordance with the following scale:

| HEARING PROTECTIVE DEVICE COMFORT RATING SCALE | | | | |
|---|---|---|---|---|
| Very Comfortable | Comfortable | Undecided | Un-comfortable | Painful |
| 0 1 | 2 3 | 4 5 6 | 7 8 | 9 10 |

The average comfort rating afforded the earplugs of the invention by the test subjects was about 3.

For comparative purposes, a similar test series was carried out with the same cadre of test subjects utilizing a commercially available multiple flange earplug of the prior art. The Maximum Comfort Test yielded an NRR value of only 16. The Maximum Attenuation Test yielded an NRR value of about 23. The average comfort rating afforded these commercial earplugs by the test subjects during the course of the Maximum Comfort Test was about 4.

Another Maximum Comfort Test was carried out with the same cadre of test subjects utilizing yet another commercially available multiple flange earplug of the prior art. The NRR value was about 13 and the average comfort rating accorded the earplugs was about 6.

Since many embodiments, modifications and variations of the present invention may be made in view of the above teachings without departing from the spirit of the invention, it will be understood that, within the scope of the appended claims, the invention may be practiced otherwise than as specifically described hereinbefore.

What is claimed is:

1. An earplug composed of a resilient polymeric material and comprising:

an elongate stalk member having a nose end;

a flange array comprising at least three hollow, rearwardly extending flange elements of substantially circular crossections and of serially increasing diameters integrally affixed to said stalk member at spaced intervals along at least a portion of the length thereof, the flange element of the smallest diameter being located at said nose end;

each said flange element being of generally hemispherical shape, comprising a thin skirt having a substantially uniform thickness of between about 0.008 inch (0.20 mm) and about 0.050 inch (1.27 mm) and being composed of a resilient polymeric material of construction having a Shore A Durometer hardness value of between about 10 and about 90;

the diameter of each portion of said stalk member underlying each skirt being such as to define an annular free space between the interior surface of said skirt and said stalk member.

2. The earplug of claim 1 wherein the spacing of said flange elements and the diameters thereof are such that a straight line of construction can be drawn which is in at least point contact with each of the flange elements of the array and that said line of construction intersects the forwardly extended centerline of said stalk member to define a relatively shallow half-angle therebetween.

3. The earplug of claim 2 wherein said half-angle is between about 10° and about 16°.

4. The earplug of claim 2 wherein said half-angle is between about 12° and about 14°.

5. The earplug of claim 1 wherein said material of construction of each of said flange elements of said array has a Shore A Durometer hardness value of between about 30 and about 60.

6. The earplug of claim 5 wherein the thickness of the skirt of each said flange element is between about 0.030 inch (0.76 mm) and about 0.012 inch (0.30 mm).

7. The earplug of claim 1 wherein said material of construction of each said skirt has a Shore A Durometer hardness value of about 40 and wherein the thickness thereof is about 0.020 inch (0.50 mm).

8. The earplug of claim 1 wherein the diameter of each portion of said stalk member underlying each skirt increases rearwardly from flange element to flange element.

9. The earplug of claim 8 wherein the resilient polymeric material of construction of said stalk member has a Shore A Durometer hardness value of less than about 50.

10. The earplug of claim 1 wherein the resilient polymeric material of construction of said stalk member has a Shore A Durometer hardness value of between about 50 and about 70.

11. The earplug of claim 1 wherein the dimension across each annular free space is at least twice the thickness of the skirt associated therewith.

12. The earplug of claim 1 wherein said stalk member extends rearwardly from the last of said flange elements to a sufficient length as to define handle means by which to manipulate the earplug.

13. The earplug of claim 12 wherein the free end of said stalk member comprises an axially oriented channel of a size adapted to receive therein an end of a length of a pliant cord acting as a tether therefor.

14. The earplug of claim 1 wherein the junction of the interior portion of the skirt of each said flange element of the array with said stalk member is of minimum radius, thereby to minimize thickening of the material of construction at said junction and to confer to said skirt the capability of manual eversion thereof to a forwardly extending conformation, whereby the interior surface of said skirt and that portion of said stalk member underlying same are exposed.

15. The earplug of claim 1 composed of a thermoplastic silicone rubber.

16. The earplug of claim 1 wherein the spacing of said generally hemispherically shaped flange elements along said stalk member is such that the trailing edge of each skirt of each flange element is at least coplanar with respect to the nose end of the succeeding flange element thereto.

17. The earplug of claim 1 wherein the spacing of said generally hemispherically shaped flange elements along said stalk member is such that the trailing edge of each skirt of each flange element slightly overlies the nose end of the succeeding flange element thereto.

* * * * *

UNITED STATES PATENT AND TRADEMARK OFFICE
CERTIFICATE OF CORRECTION

PATENT NO. : 4,867,149

DATED : September 19, 1989

INVENTOR(S) : Robert N. Falco

It is certified that error appears in the above-identified patent and that said Letters Patent is hereby corrected as shown below:

On the title page, item [22]Filed: should read -- Dec. 16, 1988--.

Signed and Sealed this

Twentieth Day of November, 1990

Attest:

HARRY F. MANBECK, JR.

*Attesting Officer*       *Commissioner of Patents and Trademarks*